(12) United States Patent
Nelagadde

(10) Patent No.: US 9,897,518 B2
(45) Date of Patent: *Feb. 20, 2018

(54) METHOD AND APPARATUS FOR MEASURING DAMPING IN A WORKPIECE

(71) Applicants: RASSINI FRENOS, S.A. DE C.V., Puebla (MX); Manoj Nelagadde, Canton, MI (US)

(72) Inventor: Manoj Nelagadde, Canton, MI (US)

(73) Assignee: RASSINI FRENOS, S.A. DE C.V., San Martin Texmelucan, Puebla (MX)

( * ) Notice: Subject to any disclaimer, the term of this patent is extended or adjusted under 35 U.S.C. 154(b) by 401 days.

This patent is subject to a terminal disclaimer.

(21) Appl. No.: 14/394,687

(22) PCT Filed: Apr. 23, 2013

(86) PCT No.: PCT/US2013/037788
§ 371 (c)(1),
(2) Date: Oct. 15, 2014

(87) PCT Pub. No.: WO2013/163175
PCT Pub. Date: Oct. 31, 2013

(65) Prior Publication Data
US 2015/0085107 A1  Mar. 26, 2015

Related U.S. Application Data

(60) Provisional application No. 61/637,060, filed on Apr. 23, 2012.

(51) Int. Cl.
H04N 9/47 (2006.01)
G01M 17/04 (2006.01)
(Continued)

(52) U.S. Cl.
CPC ............ *G01M 17/04* (2013.01); *G01M 7/025* (2013.01); *G01M 7/08* (2013.01); *G01M 11/081* (2013.01);
(Continued)

(58) Field of Classification Search
CPC ........................... G01B 11/022; G01B 11/024
See application file for complete search history.

(56) References Cited

U.S. PATENT DOCUMENTS 3,383,980 A    5/1968  Richter
5,347,190 A *  9/1994  Lewis ................. F16C 32/0455
                                                 310/68 B
(Continued)

FOREIGN PATENT DOCUMENTS

CN    100371619 C    2/2008
CN    101178349 A    5/2008
(Continued)

OTHER PUBLICATIONS

Office Action regarding related EP App. No. 11 827 617.9; dated Jan. 26, 2016; 8 pages.
(Continued)

*Primary Examiner* — Chikaodili E Anyikire
(74) *Attorney, Agent, or Firm* — Cantor Colburn LLP

(57) ABSTRACT

A method and apparatus for measuring damping of a work piece are provided. The method includes determining at least one suitable location to measure damping on the work piece, exciting the work piece at the at least one suitable location, measuring a dynamic response of the work piece at the suitable location, and calculating a damping factor and a Q factor from the dynamic response. The apparatus includes a response measurement device configured to obtain response (Continued)

data, such as displacement data and/or velocity data, used in determining the at least one suitable location to measure damping.

18 Claims, 12 Drawing Sheets

(51) Int. Cl.
| | |
|---|---|
| *G01N 29/04* | (2006.01) |
| *G01M 7/02* | (2006.01) |
| *G01M 7/08* | (2006.01) |
| *G01M 11/08* | (2006.01) |
| *G01N 21/17* | (2006.01) |
| *G01N 29/12* | (2006.01) |
| *G01N 29/44* | (2006.01) |
| *H04N 7/18* | (2006.01) |

(52) U.S. Cl.
CPC ....... *G01N 21/1702* (2013.01); *G01N 29/045* (2013.01); *G01N 29/12* (2013.01); *G01N 29/44* (2013.01); *H04N 7/183* (2013.01); *G01N 2021/1706* (2013.01); *G01N 2201/06113* (2013.01); *G01N 2291/014* (2013.01); *G01N 2291/023* (2013.01); *G01N 2291/02827* (2013.01); *G01N 2291/2696* (2013.01)

(56) References Cited

U.S. PATENT DOCUMENTS

| | | | | |
|---|---|---|---|---|
| 5,351,951 | A * | 10/1994 | Hodgetts | A63B 60/42 473/289 |
| 6,014,899 | A * | 1/2000 | Uhlig | G01H 1/003 73/11.05 |
| 6,314,813 | B1 * | 11/2001 | Uhlig | G01M 7/025 73/11.05 |
| 6,370,958 | B1 | 4/2002 | Uhlig et al. | |
| 6,382,027 | B1 | 5/2002 | Uhlig | |
| 6,489,776 | B1 * | 12/2002 | Stowe | G01R 9/00 324/118 |
| 6,505,716 | B1 * | 1/2003 | Daudi | B23H 9/00 188/250 B |
| 2007/0113678 | A1 * | 5/2007 | Baker | G01F 1/8413 73/861.357 |
| 2009/0312966 | A1 * | 12/2009 | Nobis | G01M 17/04 702/56 |
| 2010/0307248 | A1 | 2/2010 | Hayashi | |
| 2015/0062330 | A1 | 3/2015 | Nelagadde | |

FOREIGN PATENT DOCUMENTS

| | | |
|---|---|---|
| DE | 102006039536 A1 | 3/2008 |
| JP | 2000321016 A | 11/2000 |
| KR | 1020110021271 A | 3/2011 |
| KR | 1020120032895 A | 4/2012 |
| WO | 2009069670 A1 | 4/2011 |
| WO | 2012040584 A1 | 3/2012 |

OTHER PUBLICATIONS

Chinese Office Action for related Chinese Application No. 201180051363.2 dated Sep. 26, 2014; 13 pages.
International Preliminary Report on Patentability for International Application No. PCT/US2011/052999; dated Apr. 4, 2013; 5 pages.
Svend Gade et al.; "Digital Filter Techniques vs. FFT Techniques for Damping Measurements (Damping Part I)"; Technical Review, No. 1-1994; Dec. 31, 2004; 5 pages.
English Translation for Mexican Office Action for related Mexican Patent Application No. MX/a/2013/003404; dated Apr. 24, 2014, 2 pages.
English Translation of Korean Office Action for related Korean Patent Application No. 10-2013-7010219, dated Apr. 21, 2014, 4 pages.
European Search Report for related European Application No. 11827617.9, dated Feb. 18, 2014, 10 pages.
International Search Report for International Application No. PCT/US2013/037788; International Filing Date Apr. 23, 2013; 5 pages.
International Search Report; International Application No. PCT/US2011/052999; International Filing Date: Sep. 23, 2011; 6 pages.
Korean Office Action for related Korean Patent Application No. 10-2013-7010219, dated Apr. 21, 2014, 4 pages.
Mexican Office Action for related Mexican Patent Application No. MX/a/2013/003404; dated Mar. 13, 2014, 3 pages.
N. Thrane, J. Wismer, H. Konstantin-Hansen and S. Gade, "Application Note: Pratical use of the 'Hilbert transform'", Bruel & Kjaer, Dec. 1995, 2 pages.
Svend Gade and Henrik Herlufsen, "Digital Filter Techniques vs. FFT Techniques for Damping Measurements (Damping Part I)", Bruel & Kjaer, Dec. 1994, 42 pages.
Svend Gade and Henrik Herlufsen, "Digital Filter vs. FFT Techniques for Damping Measurements", Sound and Vibration, Mar. 1990, pp. 24-31.
Written Opinion for International Application No. PCT/US2013/037788; International Filing date Apr. 23, 2013; 7 pages.
Written Opinion of International Searching Authority; International Application No. PCT/US2011/052999; International Filing Date: Sep. 23, 2011; 4 pages.
Y.F. Ji and C.C. Chang, "Non Target Stereo Vision Technique for Spatiotemporal Response Measurement of Line-Like Structures", Journal of Engineering Mechanics, vol. 134, No. 6, Jun. 1, 2008, pp. 466-474.

* cited by examiner

METHOD AND APPARATUS FOR MEASURING DAMPING IN A WORKPIECE

CROSS-REFERENCES TO RELATED APPLICATIONS

This application is a 35 USC 371 application of PCT/US13/37788, filed Apr. 23, 2013 which claims the benefit of U.S. Provisional application Ser. No. 61/637,060, filed Apr. 23, 2012 which is incorporated herein by reference in its entirety.

BACKGROUND OF THE INVENTION

The following description relates to a method of measuring damping of a work piece, and in particular, a method of measuring damping to improve efficiency.

Damping generally relates to the ability of a part to absorb energy when excited. A damping measurement may be used to assess vehicle brake noise propensity and provide a useful comparison to determine work piece vibration by capturing the ability of the work piece to absorb unwanted vibration energy. Damping measurements may be referred to using different terminology including, for example, damping factor, damping ratio, quality factor ("Q factor"), loss factor, tan delta, and/or specific damping capacity.

Current methods of damping measurement may involve exciting a part using an excitation device. Damping may be measured after the excitation device strikes the part. A time and/or frequency response is then recorded using a sensor, such as an accelerometer and/or microphone. This data is processed to obtain a Q factor, which may also be referred to as a damping number. Since the damping number (Q factor) is dependent on the location on the work piece where the impulse hammer strikes, location of measurement on the work piece, and the frequency of vibration, multiple measurements at different areas of the work piece are required to arrive at an optimum location to extract the numbers used to determine the Q factor. This type of iterative process of measuring may take an unsuitable period of time to complete. For example, the iterative process may take three or four minutes. In a production or lab environment, the delay due to this measuring time may cause other delays.

In order to reduce the measurement time, measurements may be made at multiple locations simultaneously. However, this requires a large number of sensors to be placed at or near the rotor. This increases the number of measurement channels needed.

Accordingly, it is desirable to provide a method for measuring damping limited to specific areas on the work piece to reduce the measurement time.

SUMMARY OF THE INVENTION

In one general aspect, there is provided a method of measuring damping of a work piece. The method includes determining at least one location to measure damping on the work piece, exciting the work piece at the at least one suitable location, measuring a dynamic response of the work piece at the suitable location, and calculating a damping factor and a Q factor from said dynamic response.

In another general aspect, there is provided a method of measuring damping of a work piece. The method includes placing a work piece on a support, placing a displacement measuring device proximate the work piece, exciting the work piece with an excitation device, recording a dynamic response of the work piece for a predetermined amount of time, and extracting a displacement response time history of selected points on a surface of the work piece. The method further includes determining a frequency of selected vibration modes, applying a filter on the displacement response time history to extract frequencies and modes used for a damping factor and a Q factor calculation and determining nodes and/or anti-nodes of the work piece at selected frequencies. The work piece is then excited using the excitation device at the nodes and/or anti-nodes, the dynamic response time history of the work piece is recorded at the nodes and/or anti-nodes, and a damping factor and a Q factor are calculated at the nodes and/or anti-nodes.

In still another general aspect, there is provided an apparatus for measuring damping on a work piece. The apparatus includes a support surface configured to support the work piece, an excitation device configured to excite the work piece, a displacement measuring device positioned proximate to the support surface and configured to capture a dynamic motion response of the work piece, and a control unit operably connected to the displacement measuring device configured to operate the displacement measuring device and extract data obtained by the displacement measuring device.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Figure 1:
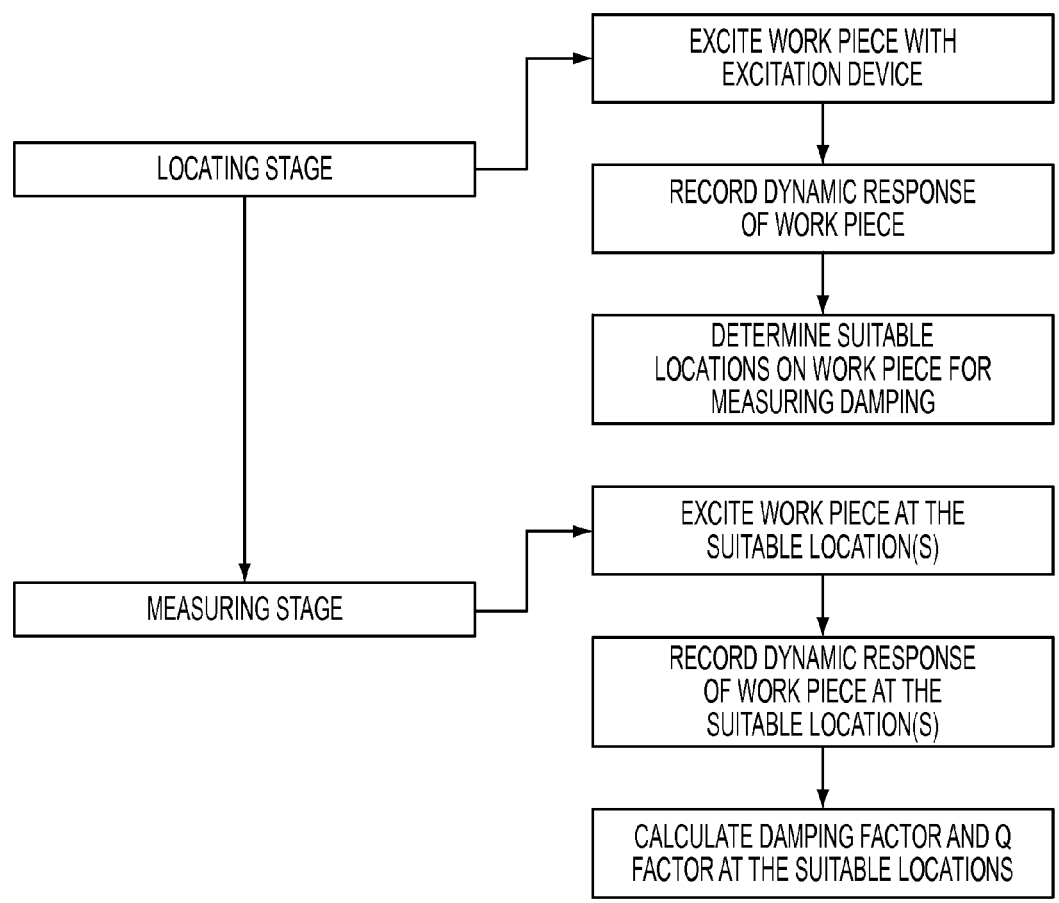
FIG. 1 illustrates a method for measuring damping on a work piece according to an exemplary embodiment of the present invention.

Referring now to the Figures, where the invention will be described with reference to specific embodiments, without limiting same, and in accordance with an exemplary embodiment of the invention, FIG. 1 is diagram showing a method of measuring damping according to an exemplary embodiment of the present invention.

Figure 2:
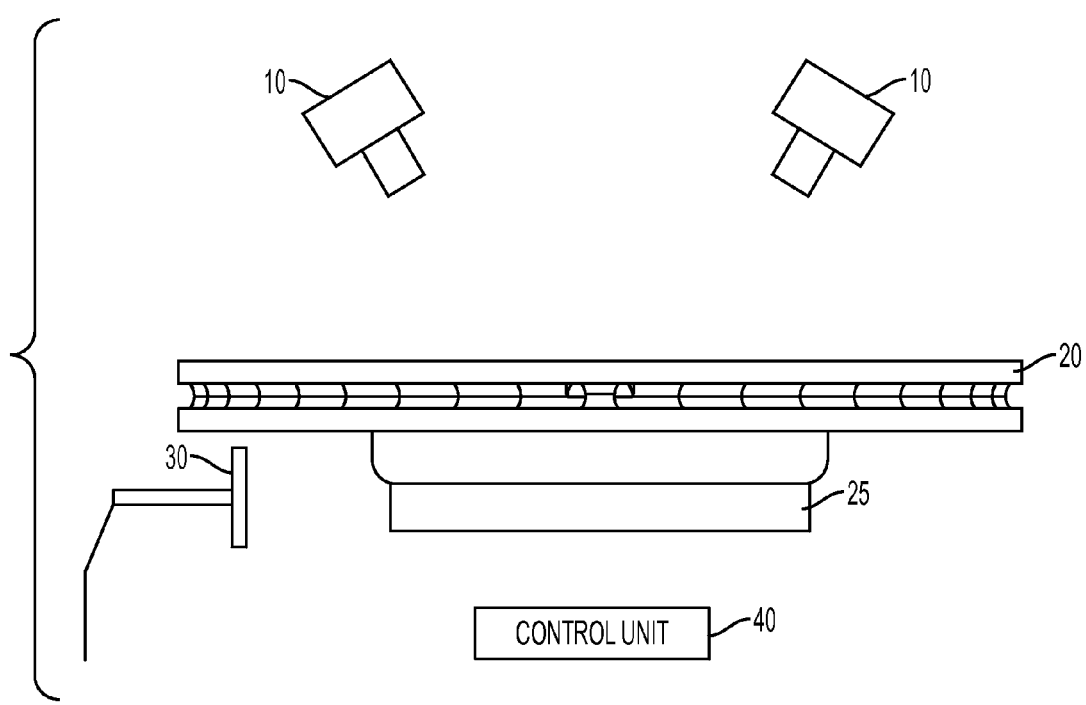
FIG. 2 illustrates a set-up for measuring the dynamic response of a work piece with high-speed cameras, according to an exemplary embodiment of the present invention.
Figure 7:
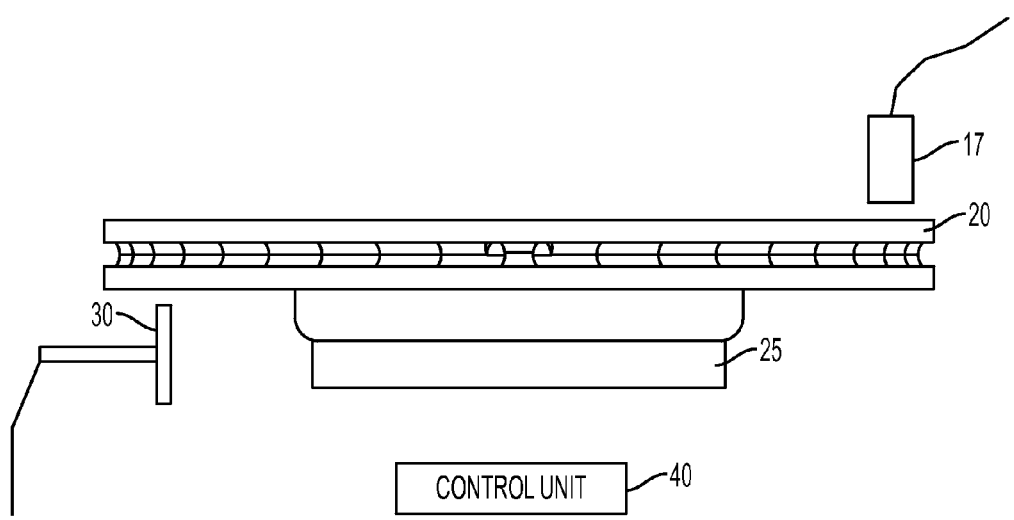
FIG. 7 shows a set-up for measuring damping factor and Q-factor of a work piece according to an exemplary embodiment of the present invention.

With reference to FIGS. 1, 2, and 7, the method generally includes two stages: A locating stage and a measuring stage. In the locating stage, a work piece 20 is excited by an excitation device 30, causing dynamic motion of the work piece 20. The dynamic motion of the work piece is captured by a response measuring device 10, 15. The response measuring device measures response data of the work piece. Response data may include, for example, the displacement, velocity and/or acceleration of the work piece 20 and various locations. Response data of the work piece 20 during the dynamic motion of the work piece 20 is either extracted or calculated from the captured dynamic motion of the work piece, or measured directly by the response measuring device 10, 15 during the dynamic motion of the work piece. A suitable location on the work piece 20 for exciting and measuring a dynamic response for determining damping of the work piece 20 at different frequencies is then determined based on the response data. A suitable location may be a node or an anti-node.

In an exemplary embodiment, the work piece 20 may be a brake rotor. However, it is understood that the work piece 20 is not limited to only a brake rotor, and may also refer to, for example, a brake drum or other component.

The response measuring device may be, for example, a camera 10, laser 15, or other suitable measurement device which can detect and measure, for example, displacement and/or velocity in an excited work piece.

In one exemplary embodiment of the present invention, the response measuring device is a camera 10. The camera 10 may be a high speed camera. With reference to FIG. 2, the high speed camera 10 is positioned proximate to the work piece 20. The high speed camera 10 captures dynamic motion of the work piece 20 after the work piece 20 is struck with an excitation device 30, such as an impulse hammer or shaker. Other suitable excitation devices may be used as well. Further, excitation of the work piece 20 may result from an outside system or component.

Figure 3:
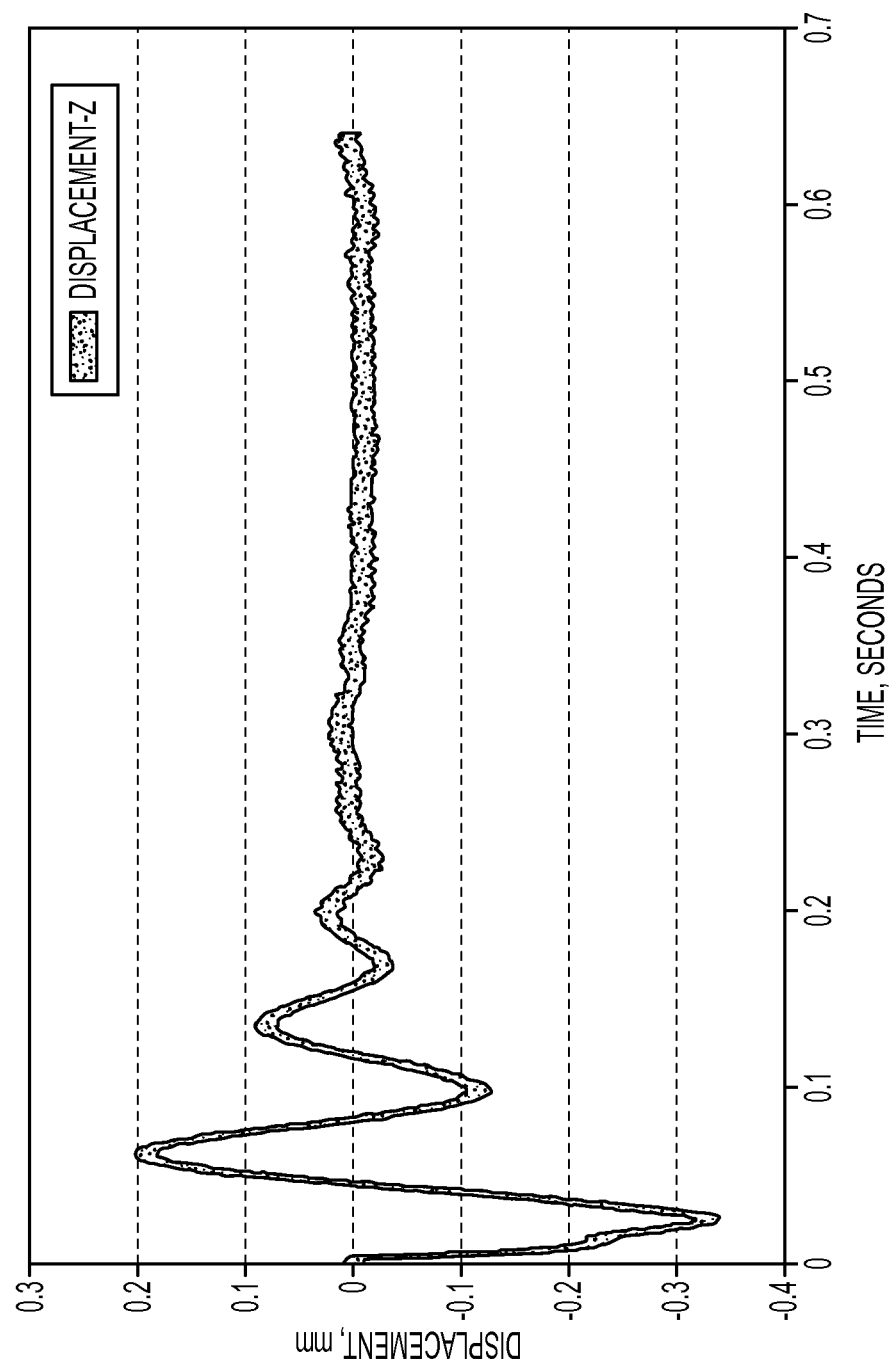
FIG. 3 illustrates a graph representing an example of displacement output generated by a digital image correlation system using cameras according to an exemplary embodiment of the present invention.

The response data obtained from the captured dynamic motion of the work piece 20 may include, among other things, displacement data of the work piece 20, for example, as shown in FIG. 3. The suitable locations, such as the nodes and anti-nodes, are determined from the displacement data. In addition, velocity and acceleration data may be determined based, in part, upon the measured displacement data.

With further reference to FIG. 3, the high speed camera 10 takes pictures of the work piece 20 at different instances of time, thereby capturing the displacement data as a function of time. This displacement data is plotted over time so a 3D dynamic displacement for the work piece movement is plotted as the work piece moves in time.

The high speed camera 10 may be operably connected to, and controlled and operated by a control unit 40 to take the pictures of the work piece 20. The control unit 40 includes a microprocessor and software stored in a memory which controls the taking of the pictures and processes the resulting data, i.e., the dynamic motion, which includes the displacement data, to obtain a 3D dynamic motion analysis of the work piece.

In an exemplary embodiment, the high speed camera 10 may include hardware and software used for operations such as taking, storing, and/or processing a picture or pictures. For example, certain software systems, such as PONTOS, ARAMIS, and VIC-3D along with camera hardware systems such as PHANTOM series from Vision Research, Inc., and FASTCAM series from Photron, Inc., may be modified to take the pictures and process a the resulting data to obtain the 3D dynamic motion analysis.

Figure 4:
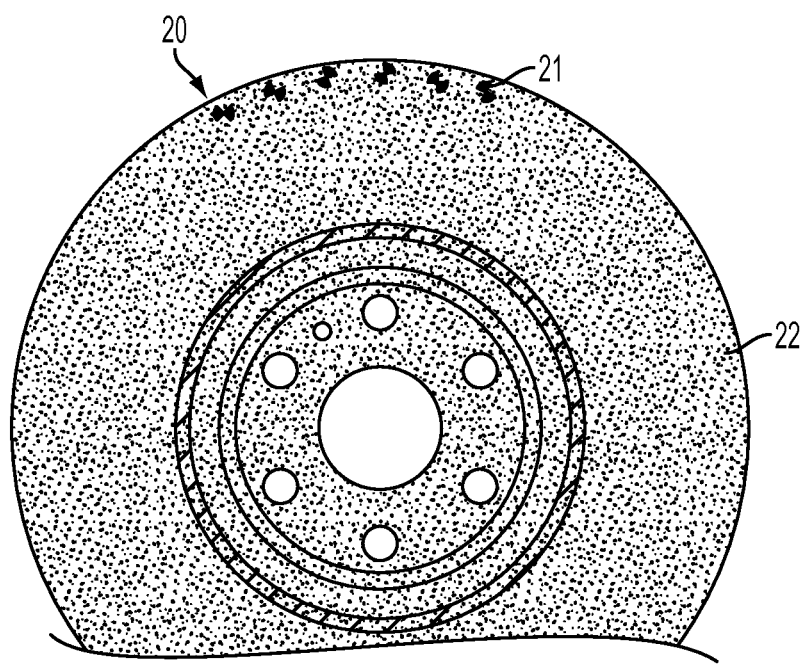
FIG. 4 illustrates a work piece with speckle pattern and markers applied according to an exemplary embodiment of the present invention.

With reference to FIG. 4, in an exemplary embodiment, markers 21 and/or speckle patterns 22 are placed on the work piece 20 to locate the different points as the work piece 20 moves. In another exemplary embodiment, a light shade may be projected to locate different points on the work piece 20 as the work piece moves.

Figure 5:
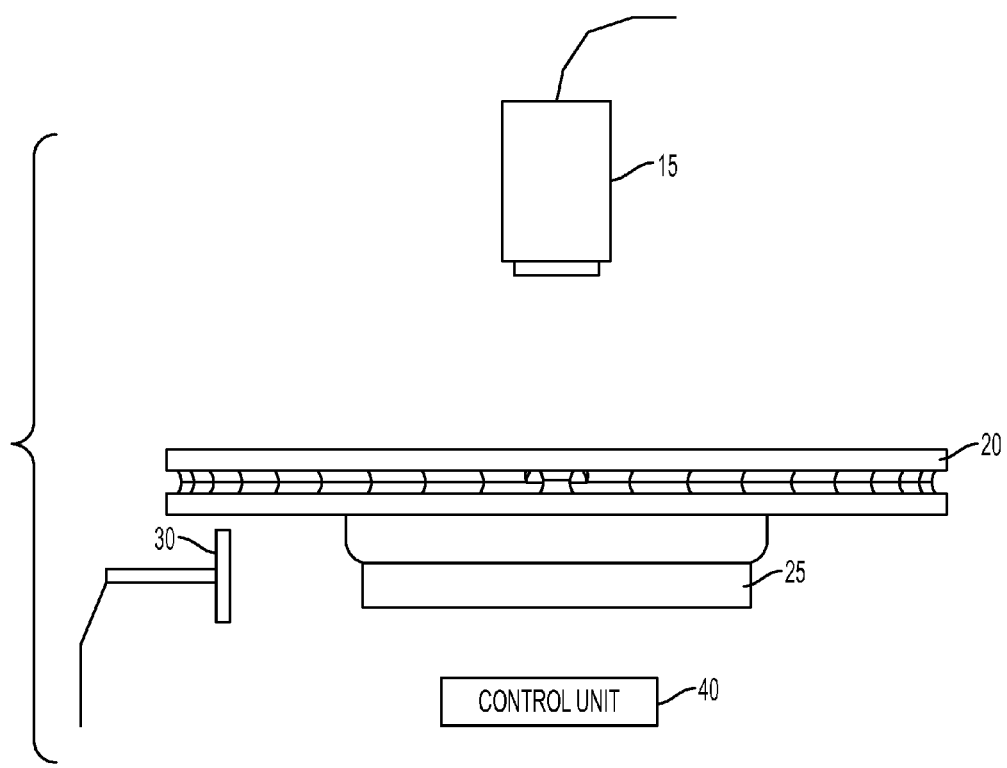
FIG. 5 illustrates a set-up for measuring dynamic response of a work piece with a scanning laser vibrometer according to an exemplary embodiment of the present invention.
Figure 6:
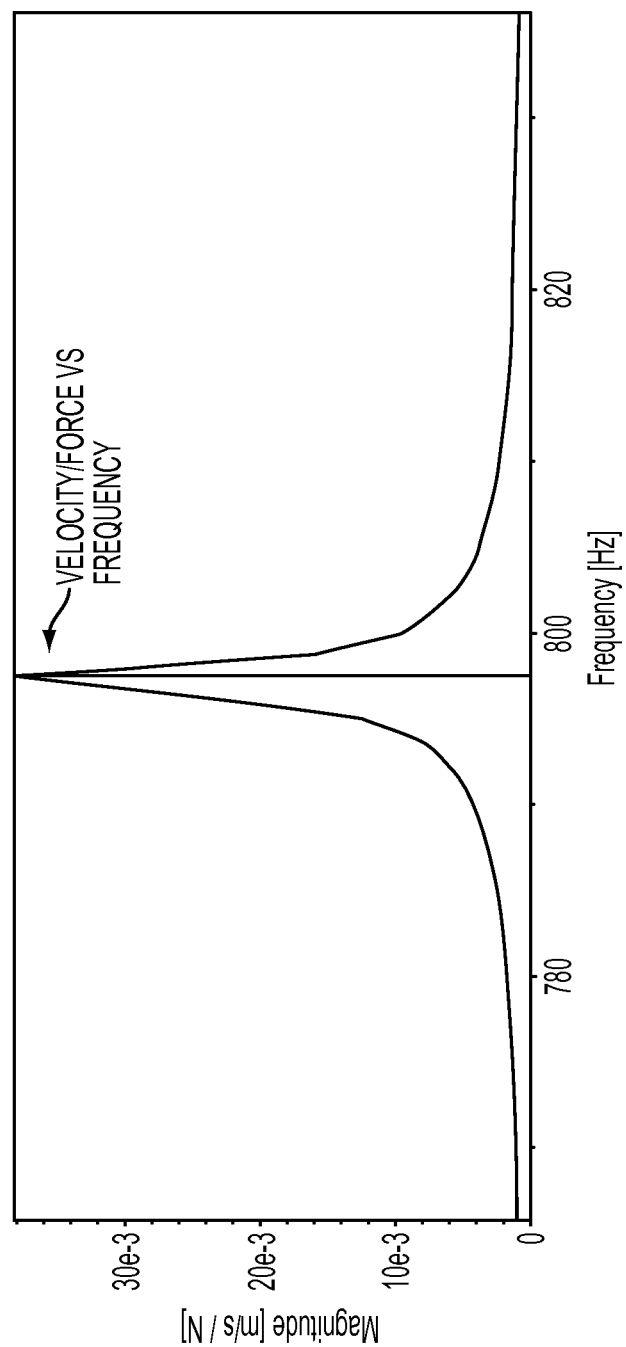
FIG. 6 graphically represents an example of velocity output generated by the scanning laser vibrometer according to an exemplary embodiment of the present invention.

With reference to FIG. 5, in another exemplary embodiment of present invention, the response measuring device may be a laser 15, for example, a scanning laser vibrometer. The scanning laser vibrometer 15 may move relative to the work piece 20, or vice versa, to capture response data from dynamic motion of the work piece 20 after the work piece 20 is struck with an excitation device 30. In an exemplary embodiment, the response data captured by the scanning laser vibrometer 15 is velocity data. The velocity data, as shown in FIG. 6, for example, is used to determine suitable locations on the work piece 20 for exciting and measuring the dynamic response of the work piece 20 to obtain damping of the work piece 20 at different frequencies. The suitable locations may be nodes and anti-nodes. It is understood that the laser vibrometer may be configured to measure displacement data instead of, or in addition to the velocity data. Acceleration data may be obtained as well. Further still, displacement, velocity or acceleration data may be determined when another of the displacement, velocity or acceleration data is measured by the laser vibrometer and other data is known, such as time.

The scanning laser vibrometer is operably connected to a control unit 40, as described above. The control unit 40 controls operation of the scanning laser vibrometer 15 and records and processes data obtained from the operation of the scanning laser vibrometer 15.

By using a scanning laser vibrometer 15 to record the dynamic motion of the work piece 20, it has been found that the dynamic response of any point on the work piece 20 may be determined in a short amount of time. The scanning laser vibrometer 15 records dynamic motion of the work piece as velocity data for a predetermined amount of time. This velocity data may be plotted over time or as a function of frequency. In an exemplary embodiment, laser vibrometer systems such as those made by POLYTEC INC can be modified to take the data and process the work piece to obtain a 3D dynamic motion analysis.

As described above, the use of a response measuring device, such as a high speed camera 10 or scanning laser vibrometer 15, allows for suitable locations on a work piece to be determined. Accordingly, in the measuring stage, where damping characteristics are measured, the measuring may be limited to the suitable locations on the work piece rather than all across the work piece 20. Thus, fewer measurements may be taken and less data needs to be analyzed, which may thereby improve efficiency. That is, only a limited number of damping measurements need to be conducted in the measuring stage after the suitable locations have been determined by the displacement measuring device.

In addition, by using a response measurement device 10, 15 to record movement of the work piece 20, as described above, multiple impacts and measurements that are required in conventional systems may be reduced or eliminated. As such, the present invention may be more practical for a production environment use.

The following steps describe one exemplary embodiment of how the suitable locations on the work piece may be determined:

Place the work piece 20 on a support 25, for example, as shown in FIGS. 2 and 5;

Position the response measuring device 10, 15 proximate to the work piece, as shown in FIGS. 2 and 5;

Excite the work piece 20 using the excitation device 30. In an exemplary embodiment, the excitation device 30 is fitted with a force transducer;

Record dynamic motion response time history of the work piece 20 after exciting the work piece 20 for a predetermined amount of time, for example, as shown in FIG. 3.

Extract the dynamic motion response time history of selected points on the surface of the work piece 20. Velocity, displacement and acceleration extracted from the software or calculated from the recorded dynamic motion response time history may also be used for further processing;

Determine the frequency of the selected vibration modes. In an exemplary embodiment, a Fast Fourier Transform (FFT) method may be used;

Apply a filter on the time data to extract the response of the frequencies and modes for the damping factor and Q factor calculations; and Determine suitable locations to measure damping, such as the nodes (minimum displacement) and anti-nodes (maximum displacement) of the work piece at selected frequencies. Record the point locations with minimum and maximum displacement magnitudes.

After the suitable locations, i.e., the nodes and/or anti-nodes, are determined in the locating stage, the damping of the work piece may be measured in the measuring stage. With reference to FIG. 7, damping may be measured using, for example, accelerometers, microphones or other sensors 17, positioned proximate to the work piece 20 and configured to measure damping at the suitable locations. The sensors are operably connected to the control unit 40, such that the control unit 40 controls operation of the sensors 17, and stores and processes data obtained by the sensors. In operation, the following steps describe a non-limiting example of how the damping may be measured once the suitable locations are determined, by calculating the Q factor and/or damping factor:

Excite the work piece 20 using the excitation device 30 at the suitable locations determined in the locating stage. In an exemplary embodiment, the excitation device 30 is fitted with a force transducer;

Record the dynamic response time history of the work piece for a predetermined amount of time; and Calculate the damping factor and the Q factor of the suitable locations based on the dynamic response of the work piece, include displacement, velocity, and/or acceleration data.

It is understood that the damping may be calculated at all or only a limited number of the suitable locations determined in the locating stage. Further, it is understood that the measuring stage may be conducted in either the same apparatus as the locating stage or a different apparatus. For example, after the locating stage, the work piece may be moved to a different apparatus for the measuring stage.

In an exemplary embodiment, the damping factor and Q factor the selected points may be calculated using one of following techniques:

a) Time domain logarithmic decrement method: Using this method, dynamic motion response data includes a decay rate of the dynamic response calculated from the time history. The Q factor and the damping factor are calculated from the dynamic response. This method is further described below.

b) Time domain envelope and decay constant calculation using Hilbert transform: In this method, an envelope of the time signal is calculated for a sinusoidal signal using a Hilbert transform and the decay rate. Q factor and damping factor are calculated from that result. This method is further described below.

c) Extract the frequency response function of the output using Fast Fourier Transform and determine modal damping factor and modal Q factor using the 3 dB method which is described below. A variation of the 3 dB method, called the ndB method, may be used instead, where "n" is any number or fraction.

d) Extract the frequency response of the output using FFT and determine the damping factor and Q factor using a modal curve-fitting algorithm/program. In a modal curve-fitting process, a theoretical curve is fit to match the measured Frequency Response Function (FRF) and the frequency, damping and mode shape are estimated. The dynamic response from an operational condition can be used instead of an external excitation of the work piece and damping may be obtained using the response or through an operational modal analysis.

e) Power Input Method (PIM): This method is based on a comparison of dissipated energy of a system to its maximum strain energy under steady state vibration, which provides frequency-averaged damping values, similar to those discussed in B. Bloss, M. D. Rao, Measurement of Damping in Structures by the Power Input Method, Experimental Techniques Volume 26, Issue 3, Pages 30-32, May 2002.

In addition to the above methods, a standard method such as an ASTM method may be applied using a test specimen instead of the work piece. It is understood that the above techniques are non-limiting examples of how the damping may be measured using the system described herein. Other suitable methods of calculation may be used as well.

Figure 8:
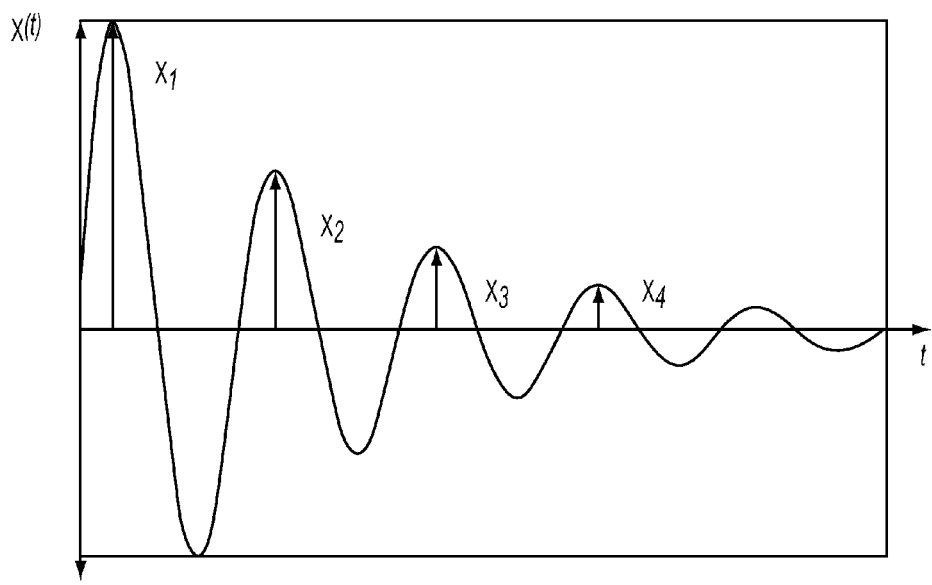
FIG. 8 illustrates a graph representing an example of a logarithmic decrement method of measuring damping factor and Q factor according to an exemplary embodiment of the present invention.

In the time domain logarithmic decrement method described above, the free vibration displacement amplitude history of a system to an impulse is measured. A free decay curve is generated, as shown in FIG. 8. The logarithmic decrement is the natural logarithmic value of the ratio of two adjacent peak values of displacement in free decay vibration as shown in FIG. 8.

Figure 9:
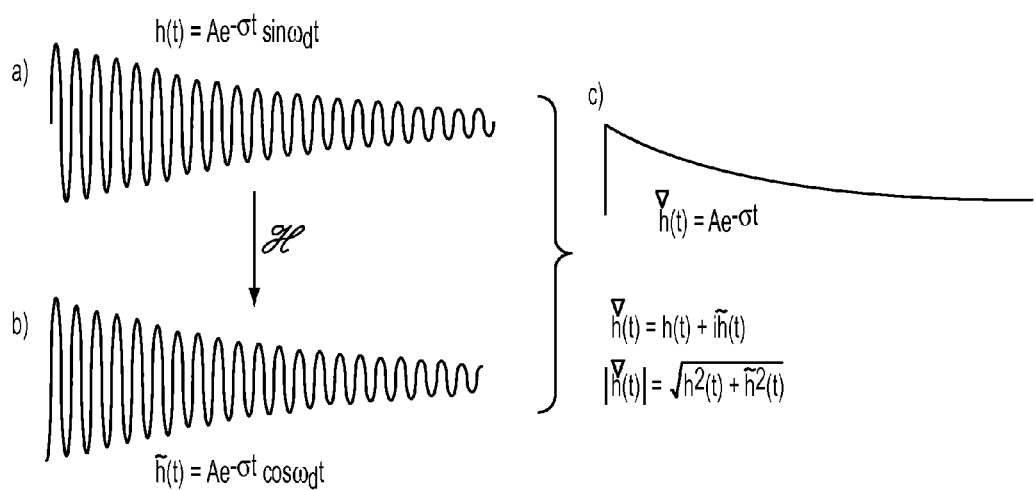
FIG. 9 illustrates graphs representing examples of a Q factor calculation using the time domain envelope decay method according to an exemplary embodiment of the present invention.

In the time domain envelope decay calculation, the signal is first filtered to extract the frequency of interest. Then, the envelope of the sinusoidal signal is extracted using a Hilbert transform. The resulting signal may be plotted on a log scale and the decay rate may be obtained from there. An example of this process is shown in FIG. 9.

A modal Q factor may be determined where the damping in the work piece 20 is a measure of the rate at which the energy is dissipated when the vibration response decays. The modal Q factor compares the frequency at which a system oscillates to the rate at which it dissipates its energy. A higher modal Q factor indicates a lower rate of energy dissipation relative to the oscillation frequency. The modal Q factor may be calculated by applying an impact force to the work piece 20 and measuring the frequency response function (FRF) of the dynamic response. That is, the modal Q factor is a specific case of the Q factor discussed above that is calculated by measuring the FRF of the dynamic response.

Figure 10:
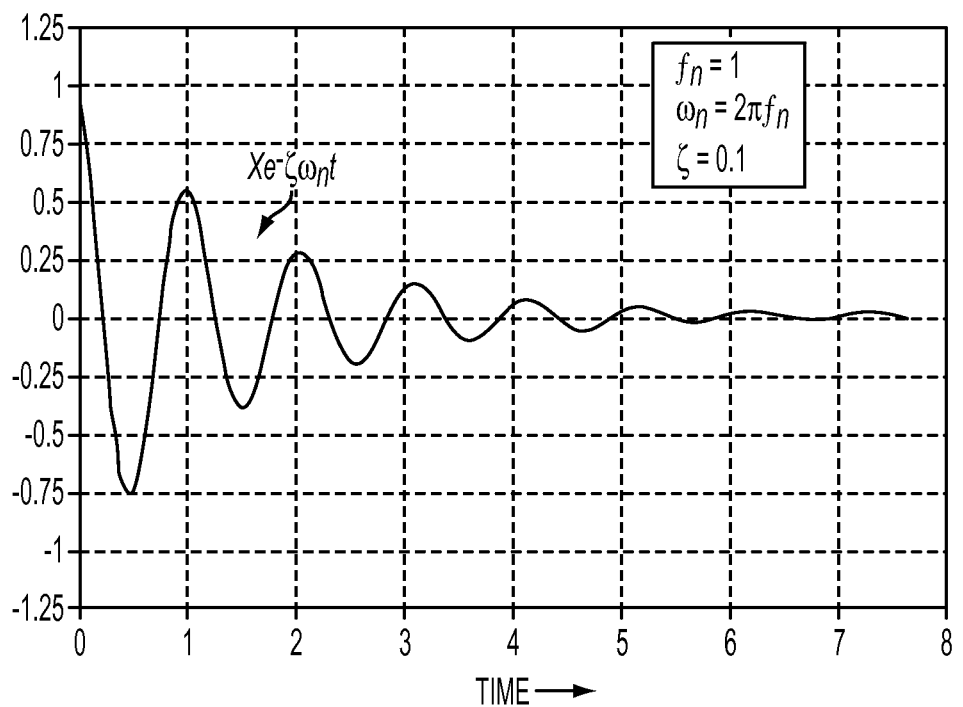
FIG. 10 illustrates a graph representing a quantified example of the decay of the response plotted over time according to an exemplary embodiment of the present invention.

FIG. 10 shows the decay of the response plotted over time. Since power and energy are proportional to the square of the amplitude of the oscillation, the bandwidth on an amplitude-frequency graph may be measured to $1/\sqrt{2}$ of the peak or approximately −3 db.

Figure 11:
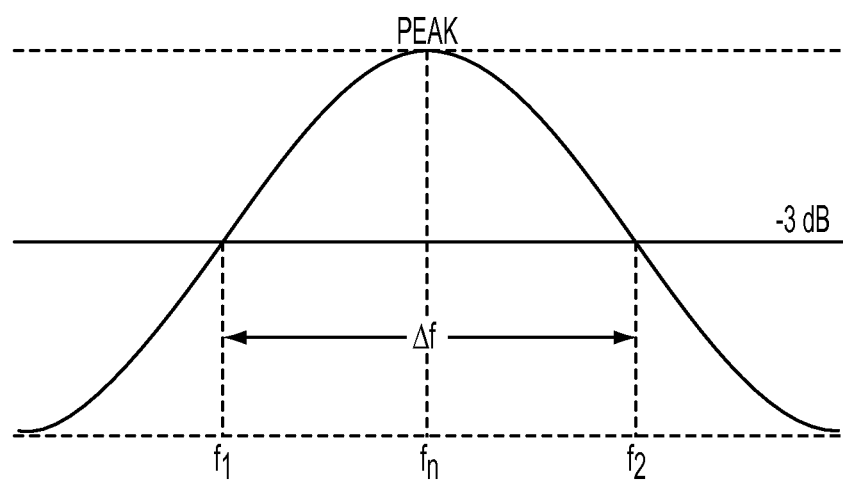
FIG. 11 illustrates a graph representing an example of a response peak and parameters used to calculate a modal Q factor according to an exemplary embodiment of the present invention.
Figure 12:
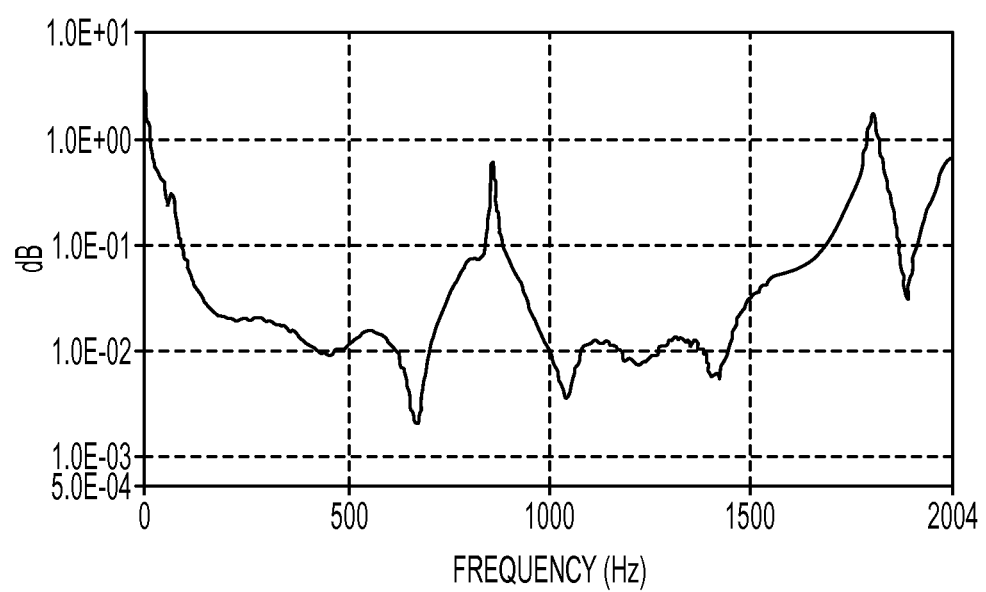
FIG. 12 illustrates a graph representing an example of a frequency response function (FRF) from which a Q factor may be calculated according to an exemplary embodiment of the present invention.

FIG. 11 shows the response peak and the parameters used to calculate Q factor. As seen in FIG. 11, "fn" is the natural frequency and f1 and f2 are the frequencies at 3 dB drop in the amplitude of the frequency response function (FRF). The width of the peak in relation to the frequency of the peak determines the Q factor and damping factor in the work piece 20. As can be seen, the higher the difference between f1 and f2, the wider the peak and the more damping in the part. FIG. 12 shows an example of a frequency response function (FRF) from which the Q factor is calculated.

$$Q = \frac{Fn}{(f1 - f2)}$$

A modal damping factor or modal damping ratio is the ratio of the damping in the work piece 20 to a critical damping value. The critical damping value is the value at which there is no oscillation and the amplitude dies down without going through any oscillation. For example:

$$\text{Damping factor } v = c/cc = \frac{c}{2\sqrt{K} \cdot \sqrt{M}}$$

where $cc = 2\sqrt{K \cdot M}$ is the critical damping value;
K is the stiffness; M is the mass; and c is the damping constant which is mathematically represented as the ratio of damping force to the velocity, which is an inherent property of a material.

Damping factor is related to the Q factor by the following formula:

$$v = \frac{1}{2Q}$$

or may be represented as a percentage by:

$$v = \frac{100}{2Q}$$

Hence, Q factor can be represented as:

$$Q = \sqrt{K} \cdot \sqrt{M}$$

where K is the stiffness, M is the mass and c is the damping constant.

The method above may be carried out at the control unit 40. The data obtained by the displacement measuring device 10, 15 and sensors 17 may be stored in the memory of the control unit 40. In addition, software may be stored in the memory of the control unit 40 as executable program instructions which are carried out by the microprocessor of the control unit 40. The calculations and methods described above may be carried out by the control unit 40 based on the data obtained from the displacement measuring device 10, 15, sensors 17, and/or other data input to the control unit 40 through an Input/Output (I/O) module.

The methods above may provide an advantage over conventional methods in that suitable locations are determined to record the dynamic response of a work piece for measuring damping of the work piece. Thus, fewer measurements are required and less data needs to be processed. That is, the above methods allow for specific points on a work piece to be identified, and then measuring the Q factor and damping factor of the specific point or points on the work piece. By measuring Q factor and damping factor only at specific points, fewer measurements may be taken, and less data needs to be processed. Thus, the measuring of the Q factor and damping factor may be done in a shorter period of time.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A method of measuring damping of a work piece comprising: determining at least one location to measure damping on the work piece based on data obtained from a single excitation of the work piece by contacting the work piece with an excitation device; exciting the work piece at the at least one suitable location with a single physical striking of the work piece by contacting the work piece with the excitation device; measuring a dynamic response of the work piece at the suitable location with a response measuring device positioned proximate to a support surface that supports the work piece, the response measuring device capturing a dynamic motion of the work piece at all locations of the work piece with the single physical striking of the work piece to determine nodes and/or anti-nodes of the work piece at selected frequencies based on data obtained from the single physical striking of the work piece; operating the response measuring device with a control unit operably connected to the response measuring device, the control unit extracting data obtained by the response measuring device; and calculating a damping factor and a Q factor from said dynamic response at all locations of the work piece with the control unit based on data obtained with the single physical striking of the work piece.

2. The method of claim 1, wherein the at least one location is a node and/or anti-node.

3. The method of claim 1, wherein the response measuring device is a camera and the response data is displacement data of the work piece.

4. The method of claim 1, wherein the response measuring device is a laser and the response data is velocity data of the work piece.

5. The method of claim 1, wherein the work piece is a brake rotor.

6. The method of claim 1, wherein the work piece is a brake drum.

7. The method of claim 1, wherein the calculating of the damping factor and the Q factor comprises calculating a damping factor and Q factor from a decay rate of the dynamic response.

8. The method of claim 1, wherein the calculating of the damping factor and Q factor comprises calculating a damping factor and Q factor based on a frequency response function.

9. The method of claim 1, wherein exciting the work piece comprises exciting the work piece with an impulse hammer.

10. The method of claim 1, wherein exciting the work piece comprises exciting the work piece with a shaker.

11. A method of measuring damping of a work piece comprising:
    placing a work piece on a support;
    placing a response measuring device proximate work piece;
    exciting the work piece with an excitation device with a single physical striking of the work piece by contacting the work piece with the excitation device;
    recording a dynamic response of the work piece for a predetermined amount of time;
    extracting a displacement response time history of selected points on a surface of the work piece;
    determining a frequency of selected vibration modes;
    applying a filter on the displacement response time history to extract frequencies and modes used for a damping factor and a Q factor calculation;
    determining nodes and/or anti-nodes of the work piece at selected frequencies based on data obtained from the single physical striking of the work piece by contacting the work piece with the excitation device;
    exciting the work piece using the excitation device at the nodes and/or anti-nodes with a single physical striking of the work piece;
    recording the dynamic response time history of the work piece at the nodes and/or anti-nodes;
    calculating a damping factor and a Q factor at all locations of the work piece with the single physical striking of the work piece.

12. The method of claim 11, including fitting said excitation device with a force transducer.

13. The method of claim 11, further comprising calculating velocity, displacement and acceleration based on the dynamic response time history.

14. An apparatus for measuring a damping on a work piece, the apparatus comprising:
    a support surface configured to support the work piece;
    an excitation device configured to excite the work piece a single time with a single physical striking of the work piece by contacting the work piece with the excitation device;
    a response measuring device positioned proximate to the support surface and configured to capture a dynamic motion response of the work piece at all locations of the work piece with the single physical striking of the work piece to determine nodes and/or anti-nodes of the work piece at selected frequencies based on data obtained from the single physical striking of the work piece; and
    a control unit operably connected to the response measuring device and configured to operate the response measuring device and extract data obtained by the response measuring device, the control unit calculating a damping factor and a Q-factor at the nodes and/or anti-nodes based on the damping data measured by the at least one sensor upon a subsequent physical striking of the work piece with the excitation device.

15. The apparatus of claim 14, wherein the response measuring device is a camera and the extracted data is displacement data.

16. The apparatus of claim 14, wherein the response measuring device is a laser and the extracted data is velocity data.

17. The apparatus of claim 14, wherein the excitation device is configured to excite the work piece at the nodes and/or anti-nodes.

18. The apparatus of claim 17, further comprising at least one sensor configured to measure damping data at the nodes and/or anti-nodes.

* * * * *